United States Patent
Hirose et al.

(10) Patent No.: US 10,013,514 B2
(45) Date of Patent: Jul. 3, 2018

(54) SIMULATION METHOD OF GRANULAR MATERIAL AND SIMULATION DEVICE THEREOF

(71) Applicant: Sumitomo Heavy Industries, Ltd., Tokyo (JP)

(72) Inventors: Ryouta Hirose, Kanagawa (JP); Daiji Ichishima, Kanagawa (JP)

(73) Assignee: SUMITOMO HEAVY INDUSTRIES, LTD., Tokyo (JP)

(*) Notice: Subject to any disclaimer, the term of this patent is extended or adjusted under 35 U.S.C. 154(b) by 238 days.

(21) Appl. No.: 15/204,767

(22) Filed: Jul. 7, 2016

(65) Prior Publication Data
US 2017/0017737 A1 Jan. 19, 2017

(30) Foreign Application Priority Data
Jul. 17, 2015 (JP) .................... 2015-143140

(51) Int. Cl.
| G06F 7/50 | (2006.01) |
| G06F 17/50 | (2006.01) |
| G06F 17/14 | (2006.01) |
| G06F 19/00 | (2018.01) |

(52) U.S. Cl.
CPC .......... *G06F 17/5009* (2013.01); *G06F 17/14* (2013.01); *G06F 19/70* (2013.01); *G06F 19/701* (2013.01); *G06F 2217/16* (2013.01)

(58) Field of Classification Search
CPC ...................................... G06F 19/70
USPC .......................................... 703/12
See application file for complete search history.

(56) References Cited

U.S. PATENT DOCUMENTS 9,309,861 B1* 4/2016 Gaul ................. F03B 13/22
9,315,663 B2* 4/2016 Appleby ............ C08L 63/00

FOREIGN PATENT DOCUMENTS

| EP | 2 369 514 A1 | 9/2011 |
| JP | 4666357 B2 | 4/2011 |
| JP | 2011-221868 A | 11/2011 |

OTHER PUBLICATIONS

Mervyn S. Paterson, A theory for granular flow accommodated by material transfer via an intergranular fluid, 1995.*
(Continued)

*Primary Examiner* — Lechi Truong
(74) *Attorney, Agent, or Firm* — Michael Best & Friedrich LLP

(57) ABSTRACT

A granular material is a simulation target, wherein a force acting on each grain is expressed by a potential dependent term and an energy dissipation term. The potential dependent term depends on an interaction potential φ between the grains. Physical quantities included in the potential dependent term are renormalization-transformed so that a hamiltonian form expressed by a kinetic energy of the each grain and a potential energy based on the interaction potential φ does not change. Physical quantities included in the dissipation term are renormalization-transformed so that a change rate of the potential dependent term and a change rate of the dissipation term become equal. Temporal development of a renormalized granular material is calculated by performing numerical integration with respect to a motion equation of each grain of the renormalized granular material.

6 Claims, 6 Drawing Sheets

(56) References Cited

OTHER PUBLICATIONS

Herrmann, "Molecular Dynamics Simulations of Granular Materials," International Journal of Modern Physics C., ISSN: 0129-1831, DOI: 10.1142/S012918319300032X, vol. 4, No. 2, pp. 309-316, Apr. 1, 1993.

Extended Search Report issued in European Patent Application No. 16176728.0, dated Jan. 3, 2017.

Keiko M. Aoki et al., "Spontaneous Wave Pattern Formation in Vibrated Granular Materials", Physical Review Letters, Nov. 11, 1996, pp. 4166-4169 (4 sheets), vol. 77, No. 20, American Physical Society, USA.

\* cited by examiner

SIMULATION METHOD OF GRANULAR MATERIAL AND SIMULATION DEVICE THEREOF

RELATED APPLICATIONS

Priority is claimed to Japanese Patent Application No. 2015-143140, filed Jul. 17, 2015, the entire content of which is incorporated herein by reference.

BACKGROUND

Technical Field

Certain embodiments of the invention relate to a method and a device that simulate a temporal change in a granular material.

Description of Related Art

In the related art, an individual element method has been widely applied to simulation of a temporal change in a granular material. Further, a simulation that employs molecular dynamics is performed with respect to fluidization of a granular material. As a related art technique, a method for calculating a behavior of a powder layer when oscillation is given to a thin powder layer through a molecular dynamics simulation has been proposed.

SUMMARY

According to an aspect of the invention, there is provided a simulation method of a granular material including the steps of: defining a granular material S which is a simulation target in which a force acting on each grain is expressed by a potential dependent term depending on an interaction potential $\phi$ between grains and a dissipation term depending on dissipation of energy; renormalization-transforming a physical quantity included in the potential dependent term of a motion equation of each grain of the granular material S so that the form of a Hamiltonian expressed by a kinetic energy of each grain of the granular material S and a potential energy based on the interaction potential $\phi$ does not change; renormalization-transforming a physical quantity included in the dissipation term so that a rate of change of the potential dependent term and a rate of change of the dissipation term based on the renormalization transformation of the physical quantities become equal to each other; and calculating temporal development of a renormalized granular material S' by assigning initial values to a position vector and a momentum vector of each grain of the renormalized particulate S' and by performing numerical integration with respect to a motion equation of each grain with a certain time interval width based on the renormalized physical quantities.

According to another aspect of the invention, there is provided a simulation device that simulates temporal development of a granular material S which is a simulation target in which a force acting on each grain is expressed by a potential dependent term depending on an interaction potential $\phi$ between grains and a dissipation term depending on dissipation of energy, the simulation device including: an input unit; an output unit; and a processing unit, in which the processing unit renormalization-transforms, with respect to physical quantities that define the granular material S input through the input unit, the physical quantity included in the potential dependent term of a motion equation of each grain of the granular material S so that the form of a Hamiltonian expressed by a kinetic energy of each grain of the granular material S and a potential energy based on the interaction potential $\phi$ does not change, renormalization-transforms the physical quantity included in the dissipation term so that a rate of change of the potential dependent term and a rate of change of the dissipation term based on the renormalization transformation of the physical quantities become equal to each other, calculates temporal development of a renormalized granular material S' by performing numerical integration with respect to a motion equation of each grain with a certain time interval width based on the renormalized physical quantities, and outputs the temporal development of the renormalized granular material S' to the output unit.

DETAILED DESCRIPTION

Figure 1:
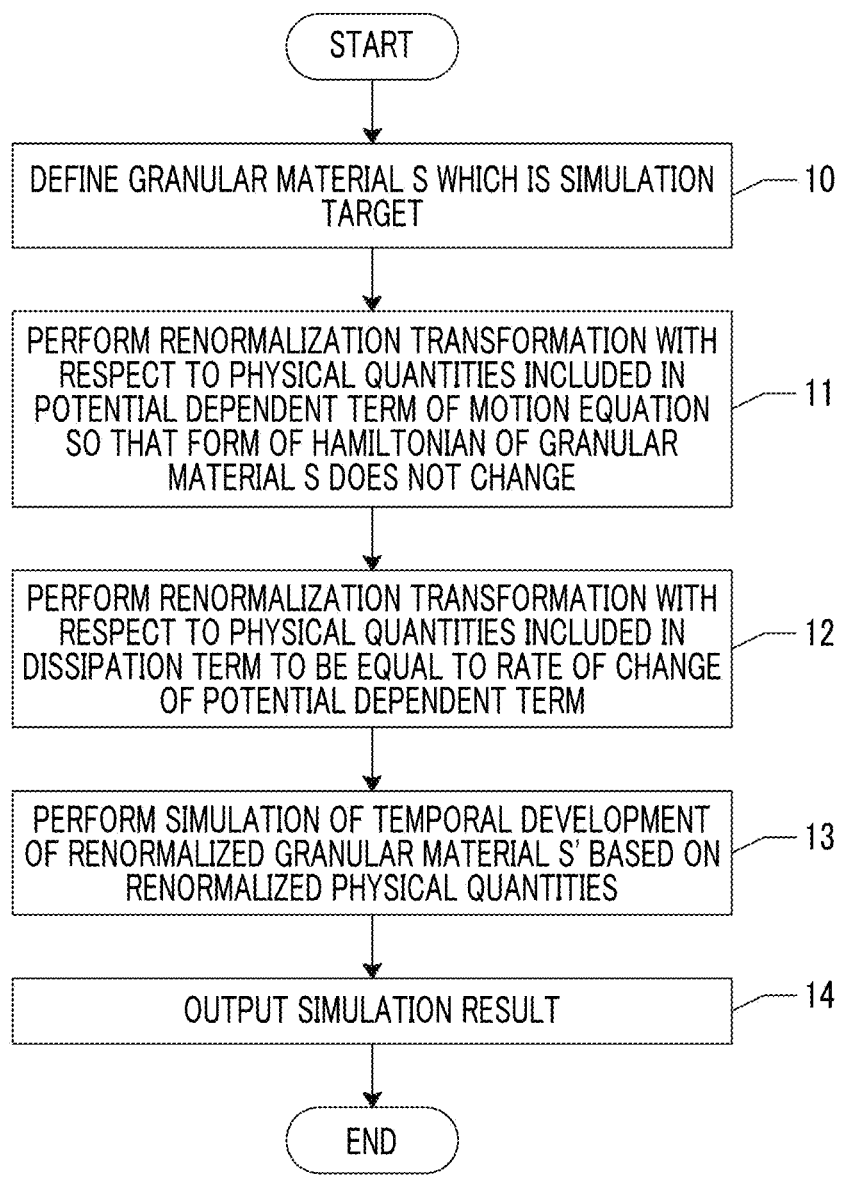
FIG. 1 is a flowchart of a simulation method according to an embodiment.

If the number of grains of a granular material which is a simulation target increases, a calculation time when simulating a macroscopic behavior becomes very long. In the related art, a renormalization group molecular dynamics method for performing renormalization group transformation with respect to a Hamiltonian capable of reducing the number of grains while maintaining the form of the Hamiltonian without change is known. If the form of the Hamiltonian does not change in the renormalization group transformation, this means that a resolution of a renormalized granular material decreases but a behavior of the renormalized granular material becomes similar to a behavior of an original granular material.

A force acting between grains applied to the molecular dynamics simulation disclosed in the related art depends on an inter-grain interaction potential. On the other hand, in a particular dynamics simulation, a force acting between grains is expressed by a term depending on an inter-grain interaction potential and a term indicating dissipation of energy. Since the force acting between grains includes the term indicating the dissipation of energy, in a case where the renormalization group transformation disclosed in the related art is applied to the particular dynamics simulation, it is not possible to secure similarity between behaviors of granular materials.

It is desirable to provide a granular material simulation method capable of reducing a calculation time of a particular dynamics simulation. Further, it is desirable to provide a granular material simulation device capable of reducing a calculation time of a particular dynamics simulation.

Since the renormalization transformation of the physical quantities included in the dissipation term is performed so that the rate of change of the potential dependent term and the rate of change of the dissipation term based on the renormalization transformation of the physical quantities become equal to each other, it is possible to simulate temporal development of a granular material including a dissipation term. Here, since the form of the Hamiltonian expressed by the kinetic energy of each grain of the granular material S and the potential energy based on the interaction potential ϕ of the granular material S does not change due to the renormalization transformation, the temporal development of the granular material S which is the simulation target and the temporal development of the renormalized granular material S are similar to each other.

Before description of a simulation method according to an embodiment, molecular dynamics applied in the simulation method according to the embodiment will be briefly described. A force $F_j$ acting on a grain j of a granular material S which is a simulation target configured by the number of grains N is expressed as the following equation.

$$\vec{F}_j = -\sum_{i \neq j}^{contact} \left[ \frac{\partial \phi(|\vec{q}_i - \vec{q}_j|)}{\partial \vec{q}_j} + c(\vec{v}_j - \vec{v}_i) \right] \quad (1)$$

Here, ϕ represents an interaction potential between grains, a vector $q_j$ represents a position vector (coordinate) of the grain j, a vector $v_j$ represents a velocity vector of the grain j, and c represents an attenuation coefficient. Σ means adding up with respect to grains which are in contact with the grain j. The first term in square brackets on the right side of Equation (1) is a potential dependent term depending on the interaction potential ϕ between grains, and the second term is a dissipation term depending on dissipation of energy. The dissipation term is expressed as a product of the attenuation coefficient c and a relative velocity of two interacting grains.

A motion equation of the grain j is obtained from the above-described Equation (1). By performing numerically integration of the motion equation with respect to each grain, temporal changes in a position vector $q_j$ and a momentum vector $p_j$ of each grain are calculated.

The interaction potential ϕ is expressed as a product εf of a non-dimensional function f depending on an inter-grain distance r and an interaction coefficient ε having a dimension of energy. The interaction potential ϕ is given as the following equation, for example.

$$\phi(r) = \varepsilon \left[ \left(\frac{\sigma}{r}\right)^{12} - \left(\frac{\sigma}{r}\right)^{6} + \frac{1}{4} \right], \left( r < r_0 = 2^{\frac{1}{6}} \sigma \right) \quad (2)$$
$$= 0, (r \geq r_0)$$

Here, r represents an inter-grain distance, and σ represents a parameter characterizing a granular material S. The first term and the second term in the square brackets of the interaction potential ϕ when satisfying $r < r_0$ in Equation (2) correspond to the Lennard-Jones potential. ¼ of the third term is a constant for smoothly connecting the interaction potential ϕ when $r = r_0$.

Next, a simulation method according to the embodiment will be described with reference to FIGS. 1 to 3C.

FIG. 1 shows a flowchart of the simulation method according to the embodiment. In step 10, a granular material S which is a simulation target is defined. Specifically, the number of grains N, a mass m of each grain, an interaction potential ϕ, an attenuation coefficient c which are physical quantities characterizing the granular material S are defined.

In step 11, the physical quantities included in the potential dependent term of the motion equation of each grain of the granular material S are renormalization-transformed so that the form of a Hamiltonian expressed by a kinetic energy of each grain of the granular material S and potential energy based on the interaction potential ϕ does not change. The renormalization transformation law is disclosed in the related art. If the form of the Hamiltonian does not change, this means that a motion of a granular material before renormalization and a motion of a granular material after renormalization are similar to each other.

For example, the number of grains N' of the renormalized granular material S', a mass m' of each grain, a position vector q' of each grain, and a momentum vector p' thereof are calculated by the following renormalization transformation law.

$$N' = \frac{N}{\alpha^d} \quad (3)$$
$$m' = m \cdot \alpha^2$$
$$\vec{q}' = \frac{\vec{q}}{\alpha}$$
$$\vec{p}' = \vec{p} \cdot \alpha$$

Here, d represents a dimensionality of a space where the granular material S is included, and α represents a renormalization factor depending on the number of renormalizations. When the number of renormalizations is n, the renormalization factor α is expressed as the following equation.

$$\alpha = 2^n \quad (4)$$

The interaction potential ϕ applied to the granular material S' renormalized by the renormalization transformation law of Equation (3) is the same as the interaction potential ϕ of the granular material S which is the simulation target. For example, before and after renormalization transformation, the interaction coefficient ε and the parameter σ included in Equation (2) do not change. If the interaction potential ϕ does not change, this means that an inter-grain distance when the original granular material S is in a stable state and an inter-grain distance when the renormalized granular material S' is in a stable state are the same. Thus, a macroscopic dimension of the renormalized granular material S' is reduced to 1/α times a macroscopic dimension of the original granular material S.

Then, in step 12, renormalization transformation is performed with respect to the physical quantities included in the dissipation term, specifically, with respect to the attenuation coefficient c and the velocity v so that a rate of change of the potential dependant term and a rate of change of the dissipation term based on the renormalization transformation of the physical quantities become equal to each other. Hereinafter, the renormalization transformation law of the physical quantities included in the dissipation term will be described.

Since the interaction potential ϕ does not change by the renormalization transformation, the potential dependent term of the motion equation does not change. That is, the rate of change of the potential dependent term based on the renormalization transformation of the physical quantities is 1. As shown in Equation (1), the dissipation term of the motion equation is expressed as the product of the attenuation coefficient c and the velocity v. As shown in Equation (3), due to the renormalization transformation, the size of the momentum vector p becomes α times, and the mass m becomes $\alpha^2$. Since the velocity v is equal to p/m, the velocity v becomes 1/α due to the renormalization transformation. In order to prevent the dissipation term expressed as the product of the attenuation coefficient c and the velocity v from changing due to the renormalization transformation, the following renormalization transformation law may be applied between the attenuation coefficient c of the granular material S and an attenuation coefficient c' of the renormalized granular material S'.

$$\vec{v}' = \frac{\vec{v}}{\alpha} \quad (5)$$
$$c' = c \cdot \alpha$$

Then, in step 13, temporal development of the renormalized granular material S' is simulated based on the physical quantities renormalized in step 11 and step 12. Specifically, initial values of the position vector q and the momentum vector p of each grain of the granular material S' are set. Numerical integration is performed with respect to a motion equation of each grain with a certain time interval width based on the renormalized physical quantities. Temporal changes in the position vector q and the momentum vector p of each grain are calculated by the above-mentioned numerical integration.

Then, in step 14, a simulation result is output. As the simulation result, the position of a grain at each time point may be displayed as an image, for example. Alternatively, a macroscopic appearance of the granular material S' may be displayed as an image.

Figure 2:
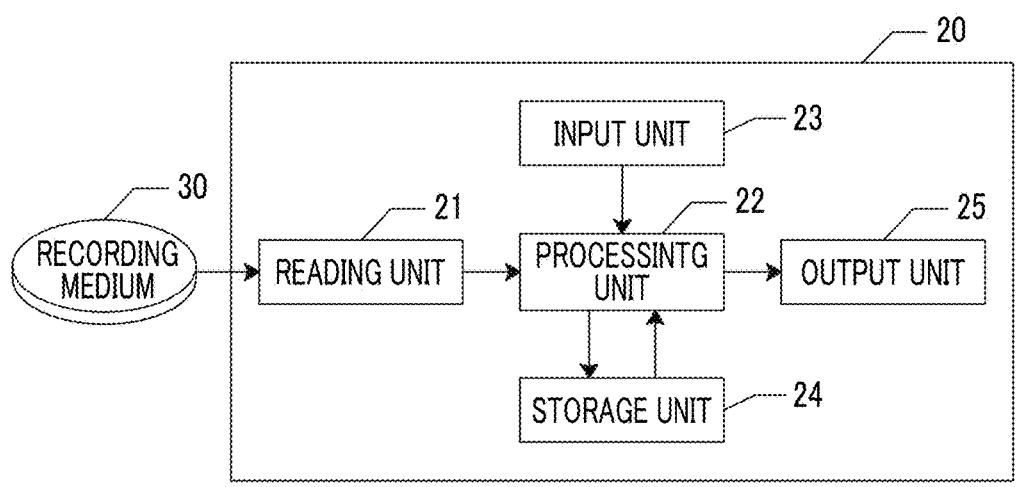
FIG. 2 is a block diagram of a simulation device (computer) that executes a simulation method according to an embodiment, and a recording medium on which a program for causing the simulation device to execute the simulation method is recorded.

FIG. 2 shows a block diagram of a simulation device (computer) that executes the simulation method according to the embodiment, and a recording medium on which a program for causing the simulation device to execute the respective steps in FIG. 1 is recorded.

A simulation device 20 includes a reading unit 21, a processing unit 22, an input unit 23, a storage unit 24, and an output unit 25. A program for causing the simulation device 20 to execute the simulation method shown in FIG. 1 is recorded on a computer-readable recording medium 30.

The reading unit 21 reads the program recorded on the recording medium 30. The read program is stored in the storage unit 24, for example, and is executed by the processing unit 22. Hereinafter, a specific procedure in steps 10 to 14 shown in FIG. 1 will be described.

In step 10 (FIG. 1), the physical quantities that define the granular material S which is the simulation target are acquired through the input unit 23. Thus, the granular material S which is the simulation target is defined.

In step 11 (FIG. 1), the number of renormalization transformations n is acquired through the input unit 23. The processing unit 22 calculates the renormalization factor α using Equation (4). Renormalization transformation of the physical quantities included in the potential dependent term of the motion equation is performed using the calculated renormalization factor α. This renormalization transformation may be performed based on Equation (3). In step 12, renormalization transformation of the physical quantities included in the dissipation term of the motion equation is performed. This renormalization transformation may be performed using Equation (5).

In step 13, the processing unit 22 executes a simulation with respect to the renormalized granular material S'. In step 14, the processing unit 22 outputs a simulation result to the output unit 25.

Next, a simulation result using the method according to the embodiment and a simulation result without performing renormalization transformation will be described with reference to FIGS. 3A to 3C while comparing the simulation results.

Figure 3A:
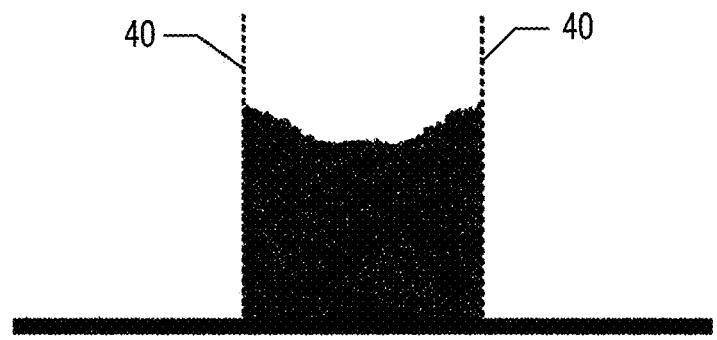
FIG. 3A is a schematic diagram illustrating an initial state of a granular material S which is a simulation target.

FIG. 3A shows an initial state of the granular material S which is the simulation target. The granular material S is placed between virtual walls 40. The virtual walls 40 form side faces of a rectangular parallelepiped that extends in a vertical direction. A mass m of each grain of the granular material S is $6.38 \times 10^{21}/N_A$ [g], an interaction coefficient ε is $6.8474 \times 10^{22}$ [K], a parameter σ that determines an interaction potential ϕ is $3.0 \times 10^{-3}$ [m], and an attenuation coefficient c is $4.2453 \times 10^4$ [kg/s]. Here, $N_A$ represents an Avogadro's constant. A space dimensionality d is 3.

Renormalization transformation is performed once with respect to the physical quantities included in the motion equation of each grain of the granular material S which is the simulation target. That is, the number of renormalization transformation n is 1, and the renormalization factor α is 2. The number of grains of the granular material S which is the simulation target is about 170,000, and the number of grains of the renormalized granular material S' is about 21,000. At a starting time of the simulation, the virtual walls 40 are removed, and then, temporal development of the granular material S and S' are calculated through simulations. At time points when the granular materials S and S' reach a normal state, the simulations are terminated.

Figure 3B:
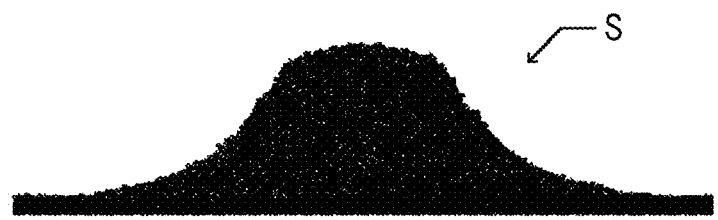
FIG. 3B is a schematic diagram illustrating a result obtained by simulating temporal development of a granular material S for which renormalization transformation is not performed.
Figure 3C:
FIG. 3C is a schematic diagram illustrating a result obtained by simulating temporal development of a renormalized granular material S'.

FIG. 3B shows a result obtained by simulating temporal development of the granular material S where renormalization transformation is not performed, and FIG. 3C shows a result obtained by simulating temporal development of the renormalized granular material S'. A macroscopic dimension of the renormalized granular material S' is reduced to ½ of the macroscopic dimension of the original granular material S, and a volume thereof is reduced to ⅛. When comparing FIG. 3B with FIG. 3C, it can be understood that the macroscopic shapes are approximately similar to each other. Accordingly, it is possible to estimate the temporal development of the original granular material S from the simulation result of the temporal development of the renormalized granular material S'.

A calculation time necessary for the simulation of the granular material S shown in FIG. 3B is about 121 hours. On the other hand, a calculation time necessary for the simulation of the renormalized granular material S' shown in FIG. 3C is about 26 hours. In this way, by performing renormalization transformation with respect to the granular material S which is the simulation target, it is possible to reduce a calculation time necessary for a simulation. If the number of renormalizations increases, it is possible to further reduce the calculation time.

Next, a simulation method according to another embodiment will be described with reference to FIGS. 4 to 7C. Hereinafter, configurations different from those of the embodiment shown in FIGS. 1 to 3C will be described, and description of common configurations will not be repeated. In this embodiment, similarly, a force Fj applied to the grain j of the granular material S is expressed as the above-mentioned Equation (1).

In the embodiment shown in FIGS. 1 to 3C, the interaction potentials φ are the same in the original granular material S and the renormalized granular material S', and the macroscopic dimension of the renormalized granular material S' is reduced to 1/α times the macroscopic dimension of the original granular material S. In this embodiment described below, the macroscopic dimension of the renormalized granular material S' and the macroscopic dimension of the original granular material S are the same, and the interaction potentials φ are different from each other. Here, in this embodiment, similarly, the form of a Hamiltonian expressed by a kinetic energy of each grain of the granular material S and potential energy based on the interaction potential φ does not change due to renormalization transformation.

Hereinafter, a renormalization transformation law applied in this embodiment will be described. The interaction potential φ applied to the granular material S which is the simulation target is defined by the following equation using a non-dimensional function f depending on an inter-grain distance r and an interaction coefficient ε.

$$\phi(r) = \varepsilon \cdot f\left(\frac{r - r_0}{\sigma}\right) \tag{6}$$

The Equation (2) may be rewritten as follows.

$$\phi(r) = \varepsilon\left[\left(\frac{1}{\frac{r-r_0}{\sigma} + \frac{r_0}{\sigma}}\right)^{12} - \left(\frac{1}{\frac{r-r_0}{\sigma} + \frac{r_0}{\sigma}}\right)^{6} + \frac{1}{4}\right], \left(r < r_0 = 2^{\frac{1}{6}}\sigma\right) \tag{7}$$

$$= 0, (r \geq r_0)$$

Accordingly, the interaction potential φ expressed by Equation (2) is also included in the interaction potential φ shown in Equation (6). Thus, the granular material S of which the interaction potential is expressed by Equation (2) may also be handled in this embodiment.

As the physical quantities characterizing the granular material S defined in step 10 (FIG. 1), a parameter $r_0$ in Equation (6) is defined, in addition to the physical quantities characterizing the granular material S defined in the embodiment shown in FIGS. 1 to 3C.

In step 11 (FIG. 1), the parameters $r_0$ and σ that regulates the number of grains N, a mass m of a grain, an interaction coefficient Σ, and a non-dimensional function f which are physical quantities that define the granular material S are transformed into parameters $r_0'$ and σ' that regulate the number of grains N', a mass m' of a grain, an interaction coefficient ε', and a non-dimensional function f' which are physical quantities that define the granular material S', respectively, by the following renormalization transformation law.

$$N' = \frac{N}{\alpha^d} \tag{8}$$

-continued $$m' = m \cdot \alpha^d$$

$$\varepsilon' = \varepsilon \cdot \alpha^d$$

$$r_0' = \alpha \cdot r_0$$

$$\sigma' = \alpha \cdot \sigma$$

The interaction potential φ' of the renormalized granular material S' may be expressed as the following equation. The form of the non-dimensional function f does not change.

$$\phi'(r) = \varepsilon' \cdot f\left(\frac{r - r_0'}{\sigma'}\right) \tag{9}$$

A Hamiltonian H' of the renormalized granular material S' may be expressed as the following equation, as described later in detail. The form of the Hamiltonian does not change due to the renormalization transformation.

$$H' = \sum_{j=1}^{N'}\left[\frac{\vec{p}_j'^2}{2m'} + \sum_{i=j+1}^{N'}\varepsilon' f\left(\frac{|\vec{q}_i - \vec{q}_j| - r_0'}{\sigma'}\right)\right] \tag{10}$$

$$\vec{p}_j' = \alpha^d \cdot \vec{p}$$

By applying the renormalization transformation law of Equation (8), the number of grains becomes $1/\alpha^d$ times, and the mass of a grain becomes $\alpha^d$ times. Thus, the entire mass of the granular material S and the entire mass of the granular material S' are the same. Further, the parameter $r_0$, that is, the inter-grain distance in a stable state becomes α times. Thus, the macroscopic dimension of the granular material S and the macroscopic dimension of the renormalized granular material S' are the same. Since the entire mass of the granular material and the dimension thereof do not change before and after the renormalization transformation process, the density of the granular material does not also change.

Next, renormalization transformation of a physical quantity included in the dissipation term performed in step 12 (FIG. 1) will be described. The potential dependent term of the motion equation is changed into the following equation.

$$\frac{\partial \phi(r)}{\partial r} = \varepsilon \cdot \frac{\partial f\left(\frac{r - r_0}{\sigma}\right)}{\partial r} \tag{11}$$

$$= \frac{\varepsilon}{\sigma} \cdot \frac{\partial f\left(\frac{r-r_0}{\sigma}\right)}{\partial \left(\frac{r-r_0}{\sigma}\right)}$$

$$= \frac{\varepsilon}{\sigma} \cdot Df$$

Here, Df is defined as the following equation.

$$Df \equiv \frac{\partial f\left(\frac{r-r_0}{\sigma}\right)}{\partial \left(\frac{r-r_0}{\sigma}\right)} \tag{12}$$

A potential dependent term of a motion equation of each grain included in the renormalized granular material S' is changed into the following equation.

$$\frac{\partial \phi'(r)}{\partial r} = \varepsilon' \cdot \frac{\partial f\left(\frac{r-r'_0}{\sigma'}\right)}{\partial r} \quad (13)$$

$$= \frac{\varepsilon'}{\sigma'} \cdot \frac{\partial f\left(\frac{r-r'_0}{\sigma'}\right)}{\partial\left(\frac{r-r'_0}{\sigma'}\right)}$$

$$= \frac{\varepsilon'}{\sigma'} \cdot Df$$

$$= \frac{\varepsilon \cdot \alpha^d}{\alpha \cdot \sigma} \cdot Df$$

The following equation is derived from Equation (11) and Equation (13).

$$\frac{\partial \phi'(r)}{\partial r} = \frac{\varepsilon \cdot \alpha^d}{\alpha \cdot \sigma} \cdot \frac{\sigma}{\varepsilon} \cdot \frac{\partial \phi(r)}{\partial r} \quad (14)$$

$$= \alpha^{d-1} \cdot \frac{\partial \phi(r)}{\partial r}$$

From Equation (14), it can be understood that the potential dependent term becomes $\alpha^{(d-1)}$ times by the renormalization transformation.

From the renormalization transformation law of the mass m of Equation (8) and the renormalization transformation law of the momentum of Equation (10), it can be understood that the velocity v does not change by the renormalization transformation. Since the velocity v included in the dissipation term of Equation (1) does not change, in order to set the dissipation term to become $\alpha^{(d-1)}$ times, the renormalization transformation law for transforming the attenuation coefficient c of the granular material S to the attenuation coefficient c' of the granular material S' may be defined as the following equation.

$$c' = c \cdot \alpha^{d-1} \quad (15)$$

Processes of step 13 and step 14 (FIG. 1) according to this embodiment are common to the processes shown in FIGS. 1 to 3C.

Next, derivation of the Hamiltonian H' (Equation 10) of the renormalized granular material S' will be described with reference to FIGS. 4 to 7. By executing a part of integration of a partition function Z(β) with respect to the granular material S to perform coarse graining with respect to a Hamiltonian, the Hamiltonian H' of the renormalized granular material S' is obtained.

The partition function Z(β) with respect to a canonical ensemble having a constant number of grains is expressed as the following equation.

$$Z(\beta) = \int d\Gamma_N \exp(-\beta H(p,q)) \quad (16)$$

$$\beta \equiv \frac{1}{k_B T}$$

Here, $d\Gamma_N$ represents a volume element in a phase space, which is expressed as the following equation.

$$d\Gamma_N = \frac{1}{W_N} \prod_{j=1}^{N} d\vec{p}_i \cdot d\vec{q}_i \equiv \frac{1}{W_N} D_p^N D_q^N \quad (17)$$

-continued $$D_p^N \equiv \prod_{j=1}^{N} d\vec{p}_i$$

$$D_q^N \equiv \prod_{j=1}^{N} d\vec{q}_i$$

$$W_N = N! \cdot h^{3N}$$

Here, h represents a Planck constant. $W_N$ is determined so that an intrinsic quantal sum of all states and integration over the phase space match each other.

First, coarse graining of an interaction potential between grains will be described, and then, coarse graining of a kinetic energy will be described. Subsequently, the renormalization transformation law is defined based on the coarse graining of the interaction potential and the coarse graining of the kinetic energy.

Coarse Graining of Interaction Potential Between Grains

First, coarse graining of an interaction potential in a granular material where grains are arranged in a one-dimensional chain pattern will be described. Then, an interaction potential in a granular material where grains are arranged in a simple cubic lattice pattern will be described.

Figure 4:
FIG. 4 is a schematic diagram illustrating a state where a grain i, a grain j, and a grain k are sequentially arranged in a one-dimensional pattern.

As shown in FIG. 4, a grain i, a grain j, and a grain k are sequentially arranged in a one-dimensional pattern. By writing an interaction relating to the grain j and executing integration with respect to position coordinates of the grain j positioned in the middle of the grain i and the grain k, it is possible to perform coarse graining of the interaction potential. First, in order to reflect contribution from a next-nearest or more distant grain, a potential moving method may be used. The potential moving method is described in "STATISTICAL PHYSICS, Static, Dynamics and Renormalization", Chap. 14, World Scientific (1999) by Leo P. Kadanoff.

An interaction potential φ Tilda in which the contribution from the next-nearest or more distant grain is reflected may be expressed as the following equation.

$$\tilde{\phi}(r) = \phi(r) + \phi(r+a) + \phi(r+2a) + \bullet\bullet\bullet \quad (18)$$

Here, a represents an inter-grain distance in an equilibrium state. The inter-grain distance a in the equilibrium state may be approximated to be equal to the distance $r_0$ where the interaction potential φ becomes a minimum.

Since plural grains are arranged in a one-dimensional pattern, the position vector $q_j$ of the grain j may be expressed as a one-dimensional coordinate. If the position of the grain j is expressed as $q_j$, a cage potential made by a nearest grain with respect to the grain j is expressed as the following equation.

$$\tilde{\phi}(q_i - q_j) + \tilde{\phi}(q_j - q_k) = \tilde{\phi}\left(\frac{q_i - q_k}{2} + \frac{q_i + q_k - 2q_j}{2}\right) + \quad (19)$$

$$\tilde{\phi}\left(\frac{q_i - q_k}{2} - \frac{q_i + q_k - 2q_j}{2}\right)$$

$$= \tilde{\phi}\left(\frac{q_i - q_k}{2} + x_j\right) + \tilde{\phi}\left(\frac{q_i - q_k}{2} - x_j\right)$$

$$= 2\left[\tilde{\phi}\left(\frac{q_i - q_k}{2}\right) + \sum_{n=1}^{\infty} \frac{1}{2n!} \tilde{\phi}^{(2n)}\left(\frac{q_i - q_k}{2}\right) x_j^{2n}\right]$$

$$x_j \equiv \frac{q_i + q_k - 2q_j}{2}$$

If integration is executed with respect to $q_j$, the following equation is obtained using Equation (19).

$$\int_{q_i+r_c}^{q_k-r_a} dq_j \exp[-\beta\{\tilde{\phi}(q_i-q_j)+\tilde{\phi}(q_j-q_k)\}] = z(q_i-q_k)P(q_i-q_k) \quad (20)$$

Here, $r_a$ represents the diameter of a grain, and $z(q_i-q_k)$ and $P(q_i-q_k)$ are expressed as the following equations.

$$P(q_i - q_k) = \exp\left[-2\beta\tilde{\phi}\left(\frac{q_i - q_k}{2}\right)\right] \quad (21)$$

$$z(q_i - q_k) = \int_{r_a-a}^{a-r_a} dx_j \exp\left[-2\beta\sum_{n=1}^{\infty}\frac{1}{2n!}\tilde{\phi}^{(2n)}\left(\frac{q_i-q_k}{2}\right)x_j^{2n}\right] \quad (22)$$

An integration region is limited to an inner region of the cage potential.

Then, $z(q_i-q_k)$ is specifically calculated. In a case where the interaction potential $\phi$ is the Lennard-Jones type potential, $\phi^{(2n)}$ is expressed as the following equation.

$$\phi^{(2n)}(r) = \frac{4\varepsilon}{\sigma^{2n}}\left[\frac{(2n+11)!}{11!}\left(\frac{\sigma}{r}\right)^{2n+12} - \frac{(2n+5)!}{5!}\left(\frac{\sigma}{r}\right)^{2n-6}\right] \quad (23)$$

In a case where the interaction potential $\phi$ is the Morse potential, $\phi^{(2n)}$ is expressed as the following equation.

$$\phi^{(2n)}(r) = \frac{\varepsilon}{\sigma^{2n}}\left[2^{2n}\exp\left(-2\frac{r-r_0}{\sigma}\right) - 2\exp\left(-\frac{r-r_0}{\sigma}\right)\right] \quad (24)$$

Numerical integration is performed by substituting Equation (23) or Equation (24) in Equation (22). When substituting Equation (23) or Equation (24) in Equation (22), Equation (18) is used. In the numerical integration, it is assumed that "a" which appears in an integration range of Equation (22) is approximately equal to $r_0$.

Figure 5:
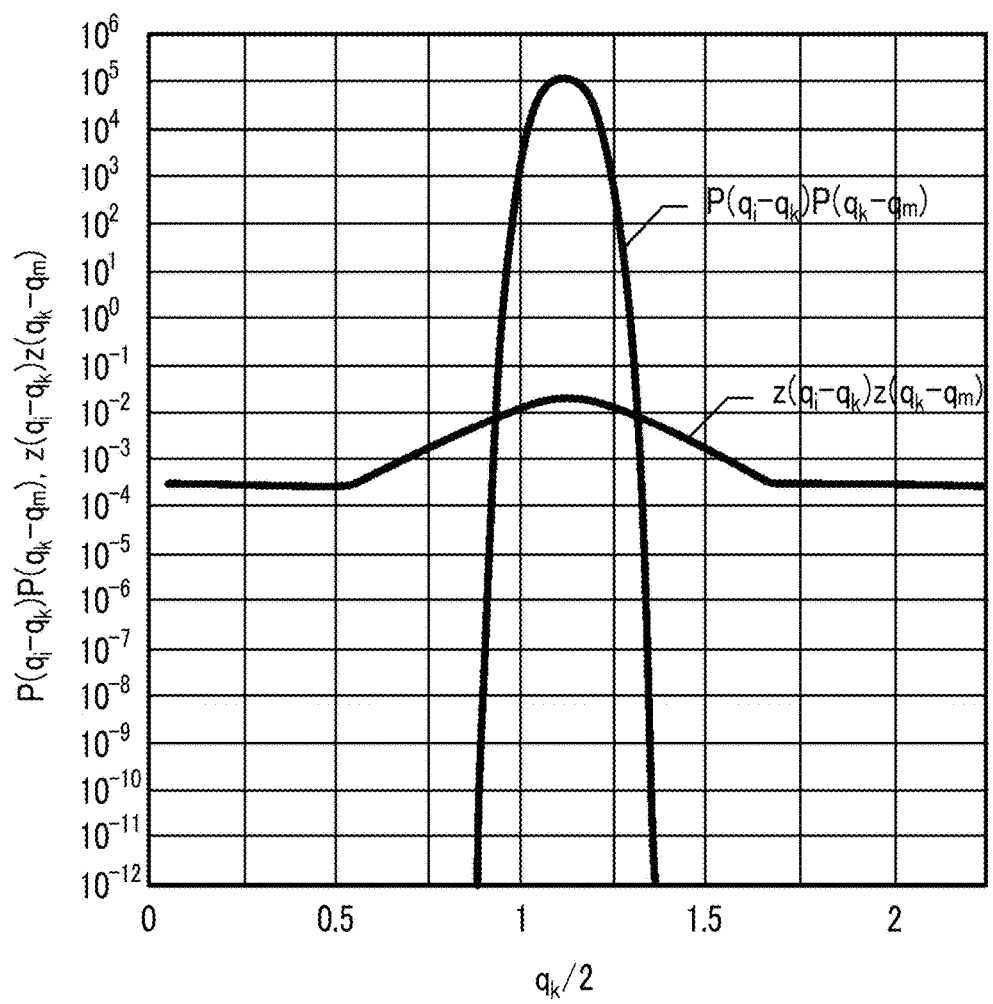
FIG. 5 is a graph illustrating a calculation result of Equation (21) and a numerical integration result of Equation (22) in a case where an interaction potential $\phi$ is a Lennard-Jones potential.
Figure 6:
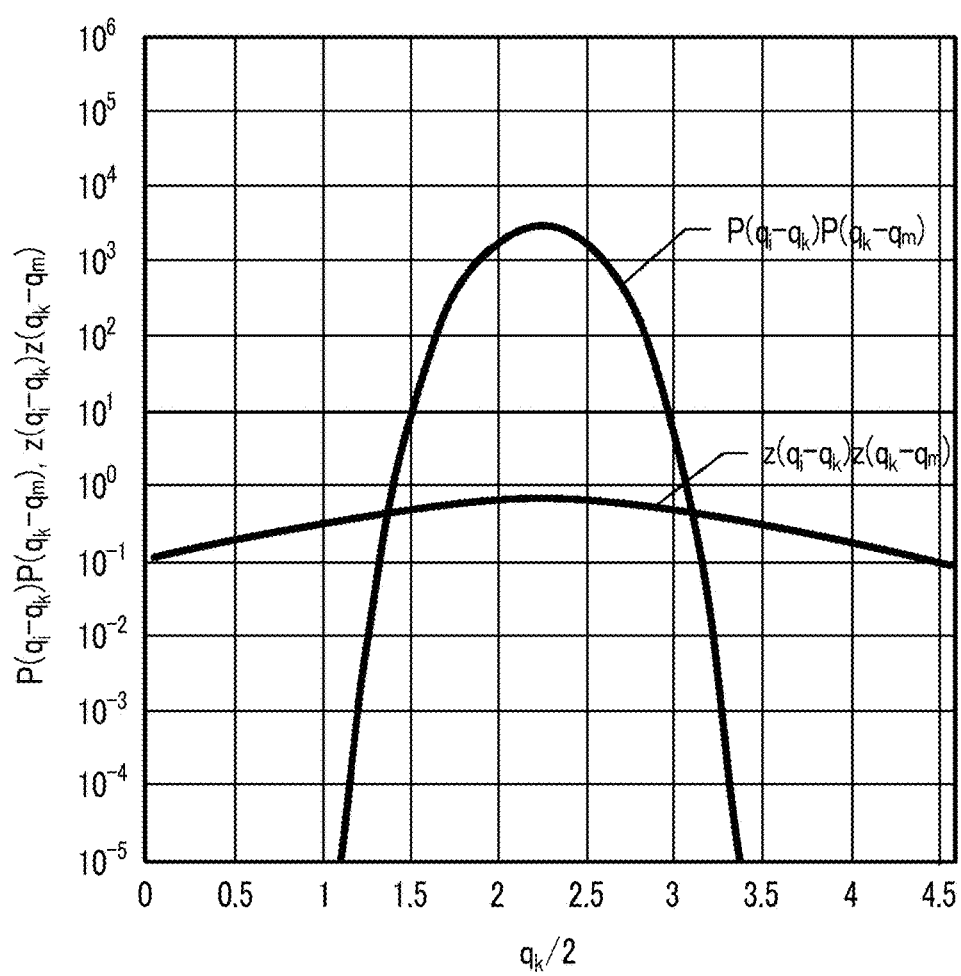
FIG. 6 is a graph illustrating a calculation result of Equation (21) and a numerical integration result of Equation (22) in a case where an interaction potential $\phi$ is a Morse potential.

FIG. 5 shows a calculation result of Equation (21) and a numerical integration result of Equation (22) in a case where the interaction potential $\phi$ is the Lennard-Jones type potential. FIG. 6 shows a calculation result of Equation (21) and a numerical integration result of Equation (22) in a case where the interaction potential $\phi$ is the Morse potential. In a case where a grain i, a grain j, a grain k, a grain l, and a grain m are sequentially arranged in a one-dimensional pattern, a position coordinate of the grain k is expressed as $q_k$. A transverse axis in FIGS. 5 and 6 represents $q_k/2$, and a longitudinal axis represents $P(q_i-q_k)P(q_k-q_m)$ and $z(q_i-q_k)z(q_k-q_m)$ in a logarithmic scale. In the numerical value calculation in FIG. 5, it is assumed that $\varepsilon/k_BT=2.0$ and $r_0/\sigma=1.12$. In the numerical value calculation in FIG. 6, it is assumed that $\varepsilon/k_BT=2.0$ and $r_0/\sigma=2.24$.

In both cases where the interaction potential $\phi$ is the Lennard-Jones type potential and where the interaction potential $\phi$ is the Morse potential, it can be understood that a change in $z(q_i-q_k)z(q_k-q_m)$ is smoother than a change in $P(q_i-q_k)P(q_k-q_m)$. Thus, $z(q_i-q_k)z(q_k-q_m)$ may be nearly approximated as a constant with respect to $P(q_i-q_k)P(q_k-q_m)$.

A probability $p(q_k)$ that the grain k is present in the position coordinate $q_k$ may be approximated as follows.

$$p(q_k) = \frac{z(q_i-q_k)z(q_k-q_m)P(q_i-q_k)P(q_k-q_m)}{\int_{q_i+r_a}^{q_m-r_a} dq_k z(q_i-q_k)z(q_k-q_m)P(q_i-q_k)P(q_k-q_m)} \quad (25)$$

$$\cong \frac{P(q_i-q_k)P(q_k-q_m)}{\int_{q_i+r_a}^{q_m-r_a} dq_k P(q_i-q_k)P(q_k-q_m)}$$

Accordingly, the following equation is derived.

$$\int_{q_i+r_a}^{q_k-r_a} dq_j \exp[-\beta\{\tilde{\phi}(q_i-q_j)+\tilde{\phi}(q_j-q_k)\}] \propto \exp\left[-2\beta\tilde{\phi}\left(\frac{q_i-q_k}{2}\right)\right] \quad (26)$$

Hereinbefore, coarse graining of an interaction potential of a granular material in which plural grains are arranged in a one-dimensional pattern is described. An interaction potential of a multi-dimensional granular material may be realized by a potential moving method.

A potential moving method for returning a two-dimensional lattice to a one-dimensional lattice will be described with reference to FIGS. 7A to 7C.

Figure 7A:
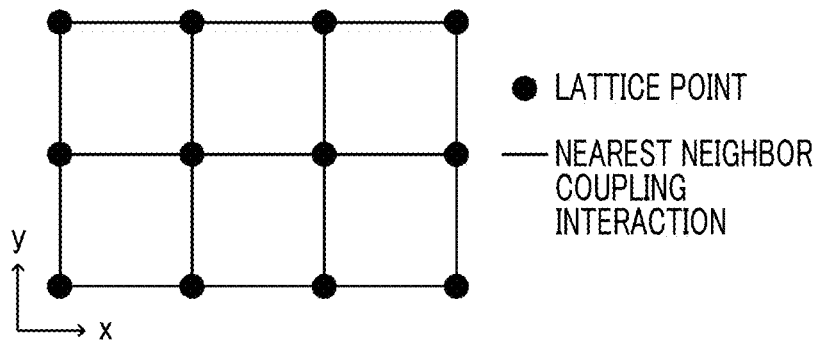
FIGS. 7A, 7B, and 7C are schematic diagrams illustrating a potential moving method for returning a two-dimensional lattice to a one-dimensional lattice.

As shown in FIG. 7A, grains are arranged at positions of lattice points of a two-dimensional square lattice. An interaction between nearest grains (nearest-neighbor-coupling) is indicated by a solid line. One direction where grains are arranged is defined as an x direction, and a direction orthogonal thereto is defined as a y direction.

Figure 7B:
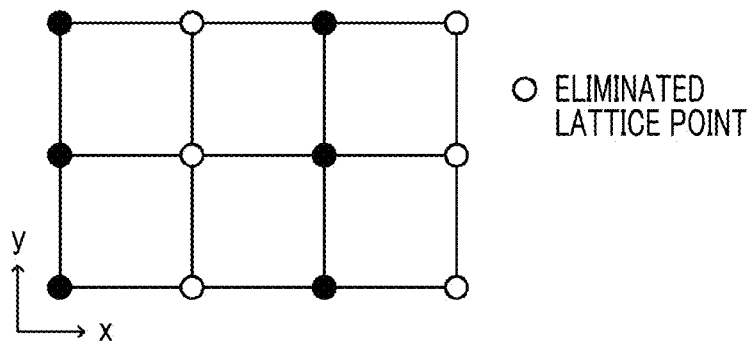

As shown in FIG. 7B, it is considered that integration is executed with respect to displacements of grains (grains indicated by hollow circles) which are alternately arranged among grains arranged in the x direction. A grain which is an integration target (a grain to be eliminated) is referred to as an integration target grain.

Figure 7C:
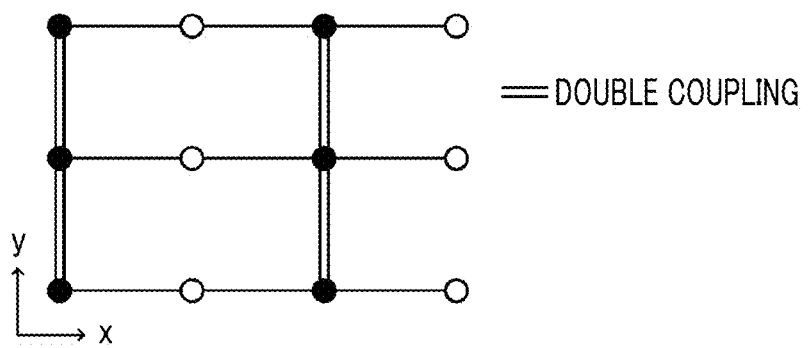

As shown in FIG. 7C, in the potential moving method, the nearest-neighbor-coupling of integration target grains is divided into grains which are adjacently arranged in the x direction. A grain interaction (double coupling) obtained by adding up divided interactions is indicated by a double-line. The double coupling indicated by the double-line has a strength two times the original nearest-neighbor-coupling. Using such a method, it is possible to transform a second-dimensional lattice into a one-dimensional chain. In the granular material of the one-dimensional chain, it is possible to perform coarse graining of an interaction potential by the method described with reference to FIG. 4. In a case where a granular material which is a simulation target forms a three-dimensional lattice, a procedure of transforming a two-dimensional lattice into a one-dimensional chain may be repeated in three directions of the x direction, the y direction, and the z direction. In this way, it is possible to perform coarse graining of a granular material that forms a multi-dimensional lattice.

Coarse graining of an interaction potential of a granular material that forms a multi-dimensional (dimensionality d) lattice is expressed as the following equation.

$$\int D_q^N \exp\left(-\beta \sum_{j=1}^{N}\sum_{i=j+1}^{N} \phi(|\vec{q}_i - \vec{q}_j|)\right) \propto \quad (27)$$

$$\int D_q^{N'} \exp\left(-\beta \sum_{\langle i,j \rangle}^{N'} 2^d \tilde{\phi}\left(\frac{|\vec{q}_i - \vec{q}_j|}{2}\right)\right)$$

$$N' = \frac{N}{2^d}$$

Here, <i, j> means that a sum is taken between nearest-neighbor lattices.

If Equation (27) is changed with respect to the sum of all interactions, the following equation is obtained.

$$\int D_q^N \exp\left(-\beta \sum_{j=1}^{N} \sum_{i=j-1}^{N} \phi(|\vec{q}_i - \vec{q}_j|)\right) \propto \int D_q^{N'} \exp\left(-\beta \sum_{j=1}^{N'} \sum_{i=j+1}^{N'} 2^d \phi\left(\frac{|\vec{q}_i - \vec{q}_j|}{2}\right)\right) \quad (28)$$

Coarse Graining of Kinetic Energy

Next, coarse graining of a kinetic energy will be described. Integration may be easily executed with respect to the kinetic energy, and accordingly, the following equation is derived.

$$\int D_p^N \exp\left(-\beta \sum_{j=1}^{N} \frac{\vec{p}_j^2}{2m}\right) \propto \int D_p^{N'} \exp\left(-\beta \sum_{j=1}^{N'} \frac{\vec{p}_j^2}{2m}\right) \quad (29)$$

In derivation of Equation (29), the following equation is used. Here, a momentum vector $p_j^2$ means an inner product of the vector.

$$\int \ldots \int d\vec{p}_i d\vec{p}_j d\vec{p}_k \ldots \exp\left(\ldots - \beta \frac{\vec{p}_i^2}{2m} - \beta \frac{\vec{p}_j^2}{2m} - \beta \frac{\vec{p}_k^2}{2m} \ldots\right) = \sqrt{\frac{2m}{\beta}} \int \ldots \int d\vec{p}_i d\vec{p}_k \ldots \exp\left(\ldots - \beta \frac{\vec{p}_i^2}{2m} - \beta \frac{\vec{p}_k^2}{2m}\right) \quad (30)$$

Derivation of Renormalization Transformation Law

Next, a renormalization transformation law derived from coarse graining of an interaction potential and coarse graining of a kinetic energy will be described.

By substituting Equation (28) and Equation (29) in Equation (16) to eliminate coefficients which do not affect a result, the following equation is obtained.

$$Z(\beta) = \int d\Gamma_{N'} \exp\left[-\beta \sum_{j=1}^{N'} \left\{\frac{\vec{p}_j^2}{2m} + \sum_{i=j+1}^{N'} 2^d \varepsilon f\left(\frac{|\vec{q}_i - \vec{q}_j| - 2r_0}{2\sigma}\right)\right\}\right] \quad (31)$$

From Equation (31), a Hamiltonian H' (Hamiltonian of the renormalized granular material S') which is subject to coarse graining is expressed as the following equation.

$$H' = \sum_{j=1}^{N'} \left\{\frac{\vec{p}_j^2}{2m} + \sum_{i=j+1}^{N'} 2^d \varepsilon f\left(\frac{|\vec{q}_i - \vec{q}_j| - 2r_0}{2\sigma}\right)\right\} \quad (32)$$

$$N' = \frac{N}{2^d}$$

A list of coupling constants when performing coarse graining of the Hamiltonian is represented as K. The list K of the coupling constants is expressed as follows.

$$K=(m,\varepsilon,\sigma,r_0) \quad (33)$$

The renormalization transformation R is defined as follows.

$$K'=R(K)=(2^d m, 2^d \varepsilon, 2\sigma, 2r_0) \quad (34)$$

A list $K_n$ of coupling coefficients after renormalization transformation is executed n times is expressed as the following equation.

$$K_n = R \circ \ldots \circ R(K) = (\alpha^d m, \alpha^d \varepsilon, \alpha\sigma, \alpha r_0)$$

$$\alpha = 2^n \quad (35)$$

Accordingly, a Hamiltonian Hn after renormalization transformation is performed n times is expressed as the following equation.

$$H_n = R \circ \ldots \circ RH \quad (36)$$

$$= \sum_{j=1}^{\frac{N}{\alpha^d}} \left\{\frac{\vec{p}_j'^2}{2\alpha^d m} + \sum_{i=j+1}^{\frac{N}{\alpha^d}} \alpha^d \varepsilon f\left(\frac{|\vec{q}_i - \vec{q}_j| - r_0 \alpha}{\sigma \alpha}\right)\right\}$$

Here, the momentum vector $p_j'$ in the renormalized granular material S' is expressed as the following equation.

$$\vec{p}_j' = \alpha^d \vec{p}_j \quad (37)$$

The renormalization transformation law shown in Equation (8) and the Hamiltonian H' of the renormalized granular material S' shown in Equation (10) are derived from Equation (36).

In this embodiment, similarly, the form of a Hamiltonian expressed by a kinetic energy of each grain of the renormalized granular material S' and potential energy based on an interaction potential ϕ is the same as the form of a Hamiltonian of the granular material S before renormalization. Thus, in this embodiment, in a similar way to the embodiment shown in FIGS. 1 to 3C, a motion of the granular material S before renormalization and a motion of the renormalized granular material S' are similar to each other.

It should be understood that the invention is not limited to the above-described embodiment, but may be modified into various forms on the basis of the spirit of the invention. Additionally, the modifications are included in the scope of the invention.

What is claimed is:

1. A simulation method of a granular material comprising:
defining a granular material S which is a simulation target in which a force acting on each grain is expressed by a potential dependent term depending on an interaction potential ϕ between grains and a dissipation term depending on dissipation of energy;
renormalization-transforming a physical quantity included in the potential dependent term of a motion equation of each grain of the granular material S so that the form of a Hamiltonian expressed by a kinetic energy of each grain of the granular material S and a potential energy based on the interaction potential ϕ does not change;
renormalization-transforming a physical quantity included in the dissipation term so that a rate of change of the potential dependent term and a rate of change of the dissipation term based on the renormalization transformation of the physical quantities become equal to each other; and calculating temporal development of a renormalized granular material S' by assigning initial values to a position vector and a momentum vector of each grain of the renormalized particulate S' and by performing numerical integration with respect to a motion equation of each grain with a certain time interval width based on the renormalized physical quantities.

2. The simulation method according to claim 1, wherein when the interaction potential $\phi$ is expressed by a product $\varepsilon f$ of a non-dimensional function f depending on an inter-grain distance and an interaction coefficient $\varepsilon$ having a dimension of energy, the dissipation term is expressed by a product of an attenuation coefficient c and a relative velocity of two grains, the number of grains of the granular material S is represented as N, the mass of each grain thereof is represented as m, a dimensionality of a space where the granular material S is included is represented as d, and a normalization factor depending on the number of renormalizations is represented as $\alpha$, the renormalization transformation is performed so that the number of grains N', a mass m' of each grain, and an attenuation coefficient c' in the renormalized granular material S' are expressed as follows, $$N' = \frac{N}{\alpha^d}$$
$$m' = m \cdot \alpha^2$$
$$c' = c \cdot \alpha.$$

3. The simulation method according to claim 1, wherein when the interaction potential $\phi$ is expressed as follows, $$\phi(r) = \varepsilon \cdot f\left(\frac{r - r_0}{\sigma}\right)$$

where f represents a non-dimensional function depending on an inter-grain distance, $\varepsilon$ represents an interaction coefficient having a dimension of energy, $r_0$ and $\sigma$ represent parameters characterizing the granular material S, and r represents the inter-grain distance, and when the dissipation term is expressed by a product of an attenuation coefficient c and a relative velocity of two grains, the number of grains of the granular material S is represented as N, the mass of each grain thereof is represented as m, a dimensionality of a space where the granular material S is included is represented as d, and a normalization factor depending on the number of renormalizations is represented as $\alpha$, the renormalization transformation is performed so that the number of grains N', a mass m' of each grain, an interaction coefficient $\varepsilon'$, and a parameter $\sigma'$ characterizing the granular material S' in the renormalized granular material S' are expressed as follows, and $$N' = \frac{N}{\alpha^d}$$
$$m' = m \cdot \alpha^d$$
$$\varepsilon' = \varepsilon \cdot \alpha^d$$
$$r'_0 = \alpha \cdot r_0$$
$$\sigma' = \alpha \cdot \sigma$$

wherein the numerical integration is performed with respect to the motion equation of each grain of the renormalized granular material S' by expressing an interaction potential $\phi'$ between grains of the renormalized granular material S' as follows, $$\phi'(r) = \varepsilon' \cdot f\left(\frac{r - r'_0}{\sigma'}\right).$$

4. A computer to execute:

a process of acquiring physical quantities by defining a granular material S which is a simulation target in which a force acting on each grain is expressed by a potential dependent term depending on an interaction potential $\phi$ between grains and a dissipation term depending on dissipation of energy;

a process of renormalization-transforming the physical quantity included in the potential dependent term of a motion equation of each grain of the granular material S so that the form of a Hamiltonian expressed by a kinetic energy of each grain of the granular material S and a potential energy based on the interaction potential $\phi$ does not change;

a process of renormalization-transforming the physical quantity included in the dissipation term so that a rate of change of the potential dependent term and a rate of change of the dissipation term based on the renormalization transformation of the physical quantities become equal to each other; and a process of calculating temporal development of a renormalized granular material S' by assigning initial values to a position vector and a momentum vector of each grain of the renormalized particulate S' and by performing numerical integration with respect to a motion equation of each grain with a certain time interval width based on the renormalized physical quantities.

5. A non-transitory computer-readable recording medium on which a program is recorded, the program causing a computer to execute:

a process of acquiring physical quantities by defining a granular material S which is a simulation target in which a force acting on each grain is expressed by a potential dependent term depending on an interaction potential $\phi$ between grains and a dissipation term depending on dissipation of energy;

a process of renormalization-transforming the physical quantity included in the potential dependent term of a motion equation of each grain of the granular material S so that the form of a Hamiltonian expressed by a kinetic energy of each grain of the granular material S and a potential energy based on the interaction potential $\phi$ does not change;

a process of renormalization-transforming the physical quantity included in the dissipation term so that a rate of change of the potential dependent term and a rate of change of the dissipation term based on the renormalization transformation of the physical quantities become equal to each other; and a process of calculating temporal development of a renormalized granular material S' by assigning initial values to a position vector and a momentum vector of each grain of the renormalized particulate S' and by performing numerical integration with respect to a motion equation of each grain with a certain time interval width based on the renormalized physical quantities.

6. A simulation device that simulates temporal development of a granular material S which is a simulation target in which a force acting on each grain is expressed by a potential dependent term depending on an interaction potential $\phi$ between grains and a dissipation term depending on dissipation of energy, the simulation device comprising:

an input unit;

an output unit; and a processing unit, wherein the processing unit renormalization-transforms, with respect to physical quantities that define the granular material S input through the input unit, the physical quantity included in the potential dependent term of a motion equation of each grain of the granular material S so that the form of a Hamiltonian expressed by a kinetic energy of each grain of the granular material S and a potential energy based on the interaction potential $\phi$ does not change, renormalization-transforms the physical quantity included in the dissipation term so that a rate of change of the potential dependent term and a rate of change of the dissipation term based on the renormalization transformation of the physical quantities become equal to each other, calculates temporal development of a renormalized granular material S' by performing numerical integration with respect to a motion equation of each grain with a certain time interval width based on the renormalized physical quantities, and outputs the temporal development of the renormalized granular material S' to the output unit.

* * * * *